(12) United States Patent
Hough et al.

(10) Patent No.: US 9,173,617 B2
(45) Date of Patent: Nov. 3, 2015

(54) METHOD FOR CONTROLLING RADIATION DOSE AND INTRAVENOUS CONTRAST DOSE IN COMPUTED TOMOGRAPHY IMAGING

(71) Applicants: David M. Hough, Rochester, MN (US); Lifeng Yu, Inver Grove Heights, MN (US); Joel G. Fletcher, Oronoco, MN (US); Cynthia H. McCollough, Byron, MN (US)

(72) Inventors: David M. Hough, Rochester, MN (US); Lifeng Yu, Inver Grove Heights, MN (US); Joel G. Fletcher, Oronoco, MN (US); Cynthia H. McCollough, Byron, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 226 days.

(21) Appl. No.: 13/654,496

(22) Filed: Oct. 18, 2012

(65) Prior Publication Data

US 2013/0101079 A1 Apr. 25, 2013

Related U.S. Application Data

(60) Provisional application No. 61/549,199, filed on Oct. 19, 2011.

(51) Int. Cl.
*A61B 6/03* (2006.01)
*A61B 6/00* (2006.01)

(52) U.S. Cl.
CPC . *A61B 6/03* (2013.01); *A61B 6/032* (2013.01); *A61B 6/481* (2013.01); *A61B 6/488* (2013.01); *A61B 6/544* (2013.01); *A61B 6/545* (2013.01)

(58) Field of Classification Search
USPC .............................................. 378/8
See application file for complete search history.

(56) References Cited

U.S. PATENT DOCUMENTS

| 7,450,983 | B2* | 11/2008 | Weiss | 600/410 |
|---|---|---|---|---|
| 2004/0114707 | A1* | 6/2004 | Bruder et al. | 378/4 |
| 2008/0232542 | A1* | 9/2008 | Lin | 378/16 |
| 2009/0252285 | A1* | 10/2009 | Shapiro et al. | 378/8 |
| 2011/0026668 | A1* | 2/2011 | Wu et al. | 378/16 |

OTHER PUBLICATIONS

Apel, et al., Pilot Multi-Reader Study Demonstrating Potential for Dose Reduction in Dual Energy Hepatic CT Using Non-Linear Blending of Mixed kV Image Datasets, Eur. Radiol., 2011, 21:644-652.

(Continued)

*Primary Examiner* — Phillip A Johnston
*Assistant Examiner* — Hsien Tsai
(74) *Attorney, Agent, or Firm* — Quarles & Brady, LLP

(57) ABSTRACT

A system and method for acquiring an image of a region of interest (ROI) of subject using a computed tomography (CT) system includes a) performing a scout scan of the subject using the CT system to yield scout data related to the ROI and b) determining an initial contrast volume form at least the scout data. The method also includes c) prescribing a scanning protocol to be implemented using the computed tomography system to image the ROI and d) determining a size of the subject about the ROI. The method further includes e) determining a computed tomography dose related to volume (CTDIvol) based on at least the size determined at step d) and f) adjusting the scanning protocol prescribed in step b) to match at least one of a desired radiation dose and a relative intravenous (IV) contrast dose to a reference CTDIvol. The method includes g) acquiring imaging data from the ROI using the CT system by using the adjusted scanning protocol.

20 Claims, 4 Drawing Sheets

(56) References Cited

OTHER PUBLICATIONS

Dorio, et al., Using a Saline Chaser to Decrease Contrast Media in Abdominal CT, AJR, 2003, 180:929-934.

Guimaraes, et al., Appropriate Patient Selection at Abdominal Dual-Energy CT Using 80 kV: Relationship Between Patient Size, Image Noise and Image Quality, Radiology, 2010, 257(3):732-742.

Marin, et al., Hypervascular Liver Tumors: Low Tube Voltage, High Tube Current Multidetector CT During Late Hepatic Arterial Phase for Detection—Initial Clinical Experience, Radiology, 2009, 251(3):771-779.

Marin, et al., Low-Tube-Voltage, High-Tube-Current Multidetector Abdominal CT: Improved Image Quality and Decreased Radiation Dose with Adaptive Statistical Iterative Reconstruction Algorithm—Initial Clinical Experience, Radiology, 2010, 254(1):145-153.

Marin, et al., 64-Section Multidetector CT of the Upper Abdomen: Optimization of a Saline Chaser Injection Protocol for Improved Vascular and Parenchymal Contrast Enhancement, Eur. Radiol., 2011, 21:1938-1947.

Nakayama, et al., Abdominal CT with Low Tube Voltage: Preliminary Observations about Radiation Dose, Contrast Enhancement, Image Quality and Noise, Radiology, 2005, 237:945-951.

Oda, et al., Indirect Computed Tomography Venography with a Low-Tube-Voltage Technique: Reduction in the Radiation and Contrast Material Dose-A Prospective Randomized Study, Journal of Computer Assisted Tomography, 2011, 35(5):631-636.

Orlandini, et al., Assessment of the Use of a Saline Chaser to Reduce the Volume of Contrast Medium in Abdominal CT, AJR, 2006, 187:511-515.

Takao, et al., Use of a Saline Chaser in Abdominal Computed Tomography: A Systematic Review, Clinical Imaging, 2009, 33(4):261-266.

Yu, et al., Automatic Selection of Tube Potential for Radiation Dose Reduction in CT: A General Strategy, Medical Physics, 2010, 37:234-243.

Yu, et al., Optimal Tube Potential for Radiation Dose Reduction in Pediatric CT: Principles, Clinical Implementations, and Pitfalls, RadioGraphics, 2011, 31:835-848.

\* cited by examiner

METHOD FOR CONTROLLING RADIATION DOSE AND INTRAVENOUS CONTRAST DOSE IN COMPUTED TOMOGRAPHY IMAGING

CROSS-REFERENCE

The present invention is based on, claims priority to, and incorporates herein by reference U.S. Application Ser. No. 61/549,199, filed Oct. 19, 2011, and entitled "METHOD FOR LOW RADIATION AND LOW INTRAVENOUS CONTRAST DOSE COMPUTED TOMOGRAPHY IMAGING."

BACKGROUND OF THE INVENTION

The field of the invention is systems and methods for computed tomography ("CT") imaging. More particularly, the invention relates to systems and methods for controlling both radiation dose and intravenous ("IV") contrast agent dose.

Despite tremendous effort in the CT community to minimize radiation dose, scanning protocols and radiation doses still vary widely among different CT practices, which poses substantial risks to patient safety. The substantial variation in protocols and radiation dose is largely attributable to the lack of an efficient and widely available approach to optimizing CT protocols.

Clinical evaluation by interpreting physicians is the most commonly used approach to determining the lowest possible radiation dose in CT protocols. To do the evaluation, one can gradually decrease the scanning technique until the image quality approaches the minimum acceptable limit. This approach requires exploratory low-dose scans on a number of patients, which is tedious and can potentially result in diagnostically compromised image. A more elegant approach is to use a noise insertion tool to simulate images at reduced dose levels from "standard dose" existing exams. A range of simulated dose levels can be generated and the diagnostic quality comparisons can be done across the same patient, removing patient-specific variables. This approach enables radiologists to determine the lowest acceptable dose level without risk of compromising a patient scan, which has been used for optimizing CT scanning protocols. Due to the proprietary nature of the CT raw data, the noise-insertion tools for clinical use have often been developed by manufacturers and distributed to very few users under research agreement. The technical details of the tools are not publicly available and the accuracy is usually out of the users' control, which makes their applications rather limited.

Even assuming that a reduced dose is appropriately selected by a clinician, the clinical value of the image may be correspondingly reduced by the introduction of additional variables to the imaging process. For example, the use of an intravenous (IV) contrast agent or the introduction of additional noise to the imaging process can drastically change the dose requirements.

Therefore, it would be desirable to have a system and method for managing the variables and interplay between selecting a desired radiation and IV contrast agent dose, while controlling against the risk of providing images that may not meet clinical needs because the dose of radiation or IV contrast agent is too low.

SUMMARY OF THE INVENTION

The present invention overcomes the aforementioned drawbacks by providing a system and method for acquiring an image of a region of interest (ROI) of subject using a computed tomography (CT) system that includes a) performing a scout scan of the subject using the CT system to yield scout data related to the ROI and b) determining an initial contrast volume form at least the scout data. The method also includes c) prescribing a scanning protocol to be implemented using the computed tomography system to image the ROI and d) determining a size of the subject about the ROI. The method further includes e) determining a computed tomography dose related to volume (CTDIvol) based on at least the size determined at step d) and f) adjusting the scanning protocol prescribed in step b) to match at least one of a desired radiation dose and a relative intravenous (IV) contrast dose to a reference CTDIvol. The method includes g) acquiring imaging data from the ROI using the CT system by using the adjusted scanning protocol.

In accordance with another aspect of the invention, a computed tomography (CT) imaging system is disclosed that includes an x-ray source configured to emit x-rays toward an object to be imaged, a detector configured to receive x-rays that are attenuated by the object, and a data acquisition system (DAS) connected to the detector to receive an indication of received x-rays. A computer system is coupled to the x-ray source and DAS and is programmed to control the x-ray source to perform a scout scan of the subject using the CT system and receive scout data related to the ROI from the DAS. The computer is further programmed to determine an initial contrast volume form at least the scout data, indicate a size of the subject about the ROI, and prescribe a scanning protocol to image the ROI. The computer is also programmed to determine a computed tomography dose related to volume (CTDIvol) based on at least the size of the subject, prescribe an updated scanning protocol that coordinates at least one of a desired radiation dose and a relative intravenous (IV) contrast dose with a reference CTDIvol, and control the x-ray source and the DAS using the updated scanning protocol to acquire imaging data from the ROI.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1A:
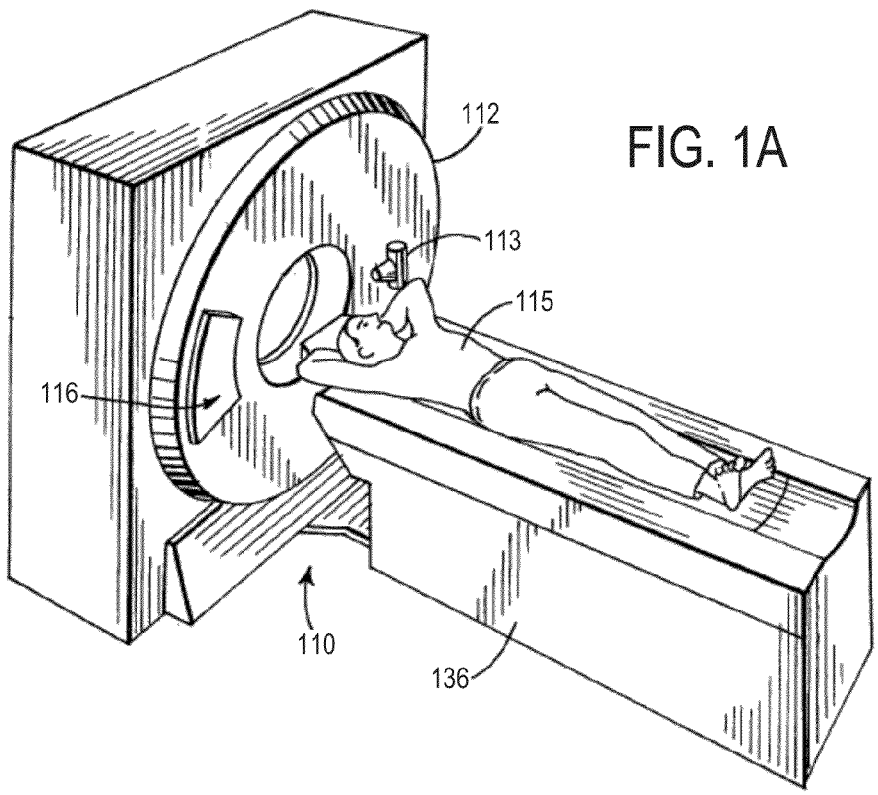
FIG. 1A is a CT imaging system in which the present invention may be employed.
Figure 1B:
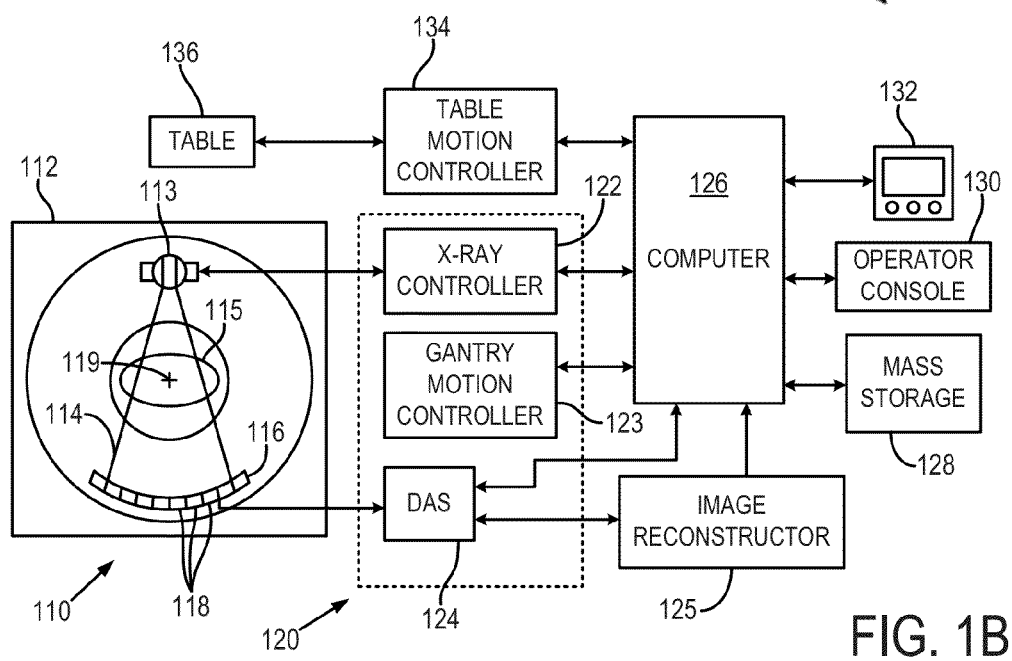
FIG. 1B is block schematic diagram of the CT imaging system of FIG. 1A.

With initial reference to FIGS. 1A and 1B, a computed tomography (CT) imaging system 110 includes a gantry 112 representative of at least a "third generation" CT scanner. In the illustrated example, the gantry 112 has a pair of x-ray sources 113 that each project a fan beam or cone beam of x-rays 114 toward a detector array 116 on the opposite side of the gantry 112. The detector array 116 is formed by a number of detector elements 118 that together sense the projected x-rays that pass through a medical patient 115. During a scan to acquire x-ray projection data, the gantry 112 and the components mounted thereon rotate about a center of rotation 119 located within the patient 115 to acquire attenuation data.

The rotation of the gantry 112 and the operation of the x-ray source 113 are governed by a control mechanism 120 of the CT system 110. The control mechanism 120 includes an x-ray controller 122 that provides power and timing signals to the x-ray sources 113 and a gantry motor controller 123 that controls the rotational speed and position of the gantry 112. A data acquisition system (DAS) 124 in the control mechanism 120 samples analog data from detector elements 118 and converts the data to digital signals for subsequent processing. An image reconstructor 125, receives sampled and digitized x-ray data from the DAS 124 and performs high speed image reconstruction. The reconstructed image is applied as an input to a computer 126 that stores the image in a mass storage device 128.

The computer 126 also receives commands and scanning parameters from an operator via console 130 that has a keyboard. An associated display 132 allows the operator to observe the reconstructed image and other data from the computer 126. The operator supplied commands and parameters are used by the computer 126 to provide control signals and information to the DAS 124, the x-ray controller 122, and the gantry motor controller 123. In addition, computer 126 operates a table motor controller 134 that controls a motorized table 136 to position the patient 115 in the gantry 112.

In CT scans, image noise is highly correlated to the dose of radiation delivered to the subject. Similarly, when a contrast agent, such as iodine is employed, the signal-to-noise ratio of the resulting image is correlated to the dose of contrast agent administered. Thus, higher SNR in a resulting image is achieved when more x-ray photons and/or a large dose of IV contrast agent are used to create the image. If a clinician were able to prospectively determine and consider whether the decreased SNR noise associated with a decreased dose of radiation or contrast agent would be acceptable to a given clinical application, the clinician would be empowered to determine whether additional dose reductions would be acceptable to the given clinical application. The present invention provides a system and method for achieving this objective.

The term "low kV CT" typically refers to imaging with CT at 100 kV, or in some cases 70 kV or 80 kV, rather than at 120 kV as is usual in CT. Low kV CT has been widely used for radiation dose reduction, especially in smaller patients, because of the benefit of increased iodine signal at lower x-ray energies. With low kV imaging, image quality equivalent to that acquired at 120 kV can be achieved with a reduced radiation dose in patients with body size less than a certain threshold.

Selection of the most appropriate kV for each patient size and diagnostic task is the subject active debate and investigation. However, taking advantage of the greater iodine signal with lower kV, the present invention makes it possible to reduce the dose of intravenous (IV) iodine contrast instead of reducing radiation dose, whilst maintaining adequate contrast. Without decreasing the radiation dose, the noise level can be controlled or maintained. Therefore, the same level of iodine contrast-to-noise ratio (CNR) can be obtained at low kV with a reduced dose of IV iodinated contrast material.

Patients who may benefit from this include those with renal insufficiency or those with poor venous access, in whom only a small IV cannula with a decreased contrast flow rate can be used. Cost savings can also be achieved from the use of low intravenous contrast dose.

In addition, an age-appropriate CT imaging method, which is designed to reduce radiation dose for younger patients and intravenous contrast dose for older patients, is provided. The present invention allows one to determine a desired radiation dose reduction in routine abdominal and pelvic CT, while maintaining sufficient diagnostic image quality. Furthermore, the present invention provides scan protocols to use in clinical practice that allow either the reduction of IV contrast dose or reduction of radiation dose, while maintaining image quality and iodine contrast-noise ratio ("iCNR"). The reduction in IV contrast dose ("IVCD") and radiation dose may be quantified, and the iCNR and IQ obtained with the new scan protocols may also be measured.

To develop the scientific basis for the present invention, a two-stage study was performed. First, the lowest acceptable radiation dose was determined. 25 lymphoma follow-up CT scans using routine dose levels (240 quality reference mAs, 120 kV) had noise inserted to simulate images at 25%, 50% and 75% dose levels. Two radiologists evaluated 4 image sets (1 randomized dose level/patient, 25 patients/set) for image quality (IQ) (scale 1-5; 3=more noise without loss of confidence, 5=normal noise, excellent IQ). The dose level yielding IQ score of 3 was selected. Second, two lymphoma follow-up CT protocols were implemented.

A first protocol was developed to reduce intravenous contrast dose (IVCD) while keeping the original radiation dose (used in patients 50 and older). The amount of IVCD reduction was determined from the lowest radiation reduction to maintain the same iodine contrast-noise ratio (iCNR). The second protocol was developed to reduce radiation dose (used in patients under 50 years). The processes used to develop both protocols employed a size-specific kV selection. 60 patients underwent follow-up CT with either reduced radiation dose (if <50 years) or reduced IV contrast dose (if 50 years). Noise, liver and aortic iCNR, and IQ (same scale) were compared to prior studies.

In the first phase, we determined by how much we could reduce radiation dose in routine CT scans of the abdomen and pelvis scans, while still maintaining diagnostic image quality. The lowest acceptable radiation dose corresponds to the iCNR that was sufficient to reliably result in diagnostic image quality. In the second phase, we developed CT acquisition protocols that allowed us to reduce radiation dose or IV contrast amount whilst maintaining this iCNR, then evaluated these protocols in our clinical practice. For both phases of the study, we selected the diagnostic task of "lymphoma follow-up" CT, as numerous exams are often performed in the same individuals for this purpose.

First Phase

To develop new low-dose protocols for following patients with lymphoma, we first needed to determine how much radiation dose we could reduce in routine CT scans of the abdomen and pelvis scans while still maintaining sufficient diagnostic image quality. In order to develop new scan protocols, in the first phase of the study, we first took 25 abdomen/pelvis scans that had been scanned with routine abdomen/pelvis technique (120 kV, 240 quality reference mAs). Raw data was exported to an off-line workstation and noise was inserted to simulate 75%, 50%, and 25% of the original radiation dose level, using a previously validated noise insertion tool. Images at different dose levels were reconstructed with 5 mm slice thickness and B40 kernel. This resulted in a total of 100 data sets, consisting of 25 patients each with 4 dose levels. These were formed into 4 groups of 25 cases, with one randomly chosen data set from each of the 25 patients being put into each of the 4 groups, so that each group consisted of 25 patients with scans from any 1 of the 4 dose levels. The cases were stripped of patient identifiers, coded and transferred to an independent workstation for viewing. The cases were independently read by 2 radiologists, reading no more than 50 cases at a time (2 groups of 25), with at least 2 weeks between reading the first 50 and the second 50 cases to minimize recall bias. Readers were blinded to the technical parameters of each scan, as well as to the clinical data and final radiologic diagnosis. For each case, the readers recorded their assessment of image quality on a 5 point scale, reflecting the readers ability to confidently diagnose or rule out pathology in the liver, spleen, kidneys, pancreas, aorta, and lymph nodes, as follows:

1: Poor image quality, not diagnostically acceptable for interpretation;

2: Suboptimal image quality, worse than routine dose images with excessive image noise, may miss lesions or mischaracterize lesions, confidence affected negatively;

3: Markedly increased noise but acceptable image quality for diagnostic interpretation, confidence not affected;

4: Good image quality, with only mild noise increase/texture change compared to routine dose images; and 5: Excellent image quality, normal image noise.

Objective evaluations of image noise were performed by region-of-interest (ROI) analysis on the standard-dose scans and simulated CT data sets. The objective image noise (SD of mean CT number) was measured by placing circular ROIs of 20-48 mm² area in the subcutaneous fat and the fluid within the urinary bladder in patients in whom the urinary bladder was not collapsed or in the gallbladder in patients in whom the urinary bladder is collapsed. The ROI locations on the standard CT scans was carefully matched to the ROIs on the corresponding simulated CT data set.

The lateral width of each patient's abdomen was measured skin to skin in cm at the level of mid portion of the liver, in order to help understand the impact of patient body habitus on dose reduction and image quality. While the lateral width information is useful, the analysis on the impact of patient body habitus on dose reduction and image quality is not required for the first phase.

Using a validated noise insertion program, noise was inserted into 25 contrast-enhanced abdomen/pelvis scans using our routine technique (120 kV, 240 quality reference mAs) to simulate 75%, 50%, and 25% of the original radiation dose level. Two radiologists, blinded to dose level and diagnosis, independently evaluated 4 randomized image sets (1 randomized dose level/patient, 25 patients/set) and recorded their assessment of image quality (IQ) on a 5 point scale reflecting the reader's ability to confidently diagnose or rule out pathology in the liver, spleen, kidneys, pancreas, aorta, and lymph nodes, as follows: 1, poor IQ, not acceptable for interpretation; 2, suboptimal IQ, excessive noise, may miss or mischaracterize lesions, confidence affected negatively; 3, Markedly increased noise but acceptable IQ for diagnostic interpretation, confidence not affected; 4, Good IQ, mild noise increase; 5, excellent IQ, normal noise. Objective noise measurements (SD of mean CT number) were also taken using region-of-interest (ROI) analysis. The ROI's on the routine dose exam were carefully matched to the ROI's on the corresponding lower-dose simulated CT exam.

Figure 3:
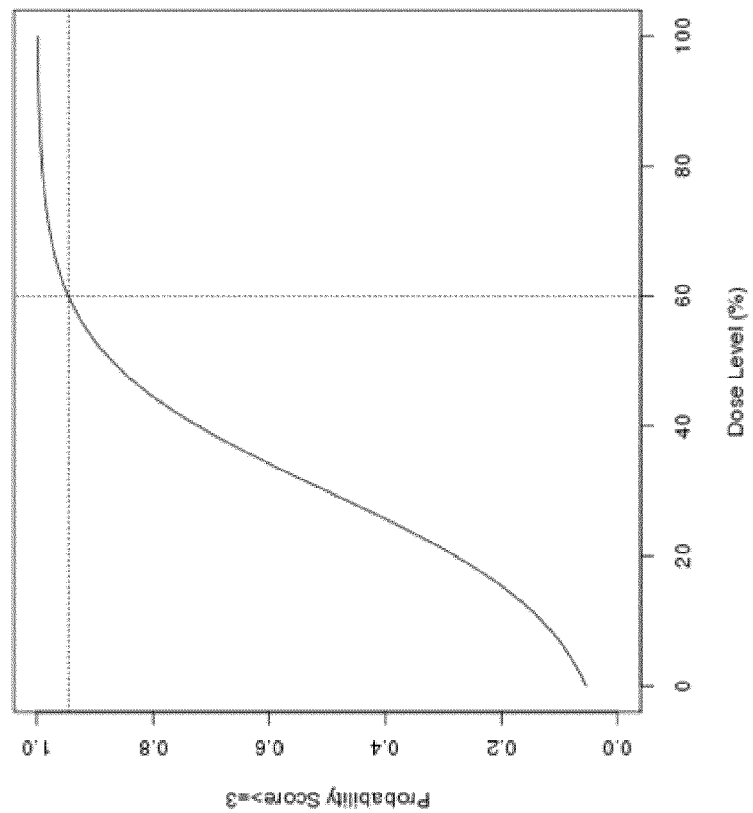
FIG. 3 is a logistic regression curve predicting a IQ score of 3 or greater based on dose level.
Figure 2:
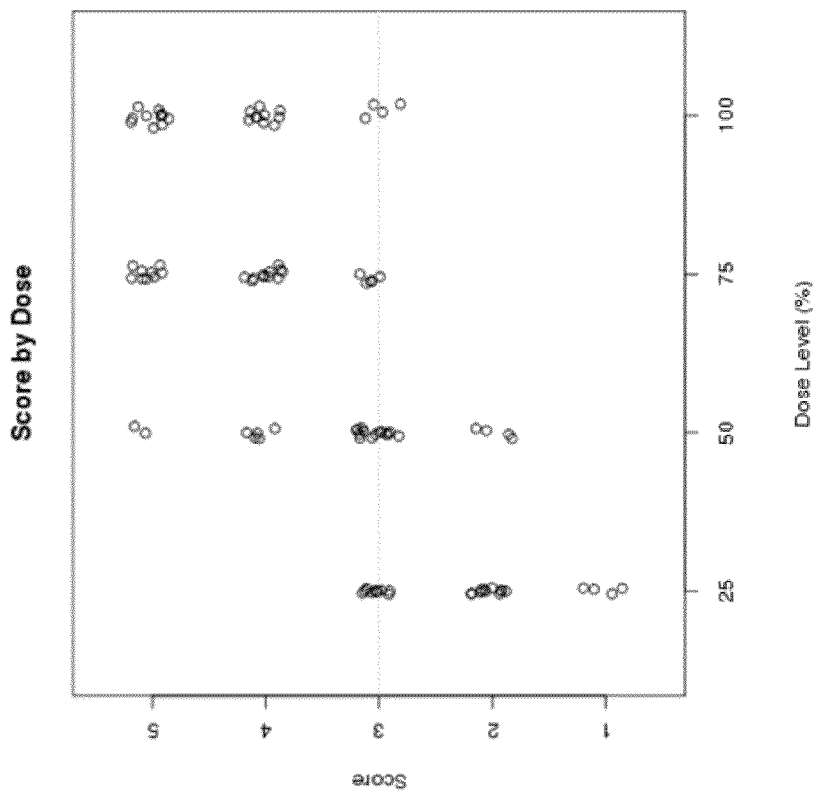
FIG. 2 is a jitter plot of IQ score by dose level.

At 50% radiation dose reduction from baseline, radiologists rated 100% and 90% of cases to have IQ score (Median 4 and 3), as illustrated in FIG. 2. We chose a 40% dose reduction to represent the iodine contrast-to-noise ratio (iCNR60%) that should be maintained, based on the logistic regression curve showing a 94% probability of an IQ score with this dose level, as illustrated in FIG. 3.

Second Phase

Protocol 1, Patients ≥50 Years

The first protocol developed was focused on reducing or lowering intravenous contrast dose (IVCD), with no change to original radiation dose. The amount of intravenous contrast dose (IVCD) reduction was determined from the lowest radiation reduction necessary to maintain the same iCNR, as outlined in Table 1 below. Baseline IVCD was calculated according to our default weight-based protocol using Iohexol 300 (Omnipaque 300, GE Healthcare Inc, Princeton N.J.).

TABLE 1

| Patient lateral width (cm) - mid liver | Optimal kV | Lowest relative IV contrast |
|---|---|---|
| 23-29 | 80 | 0.64 |
| 30-35 | 100 | 0.68 |
| 36-41 | 100 | 0.74 |
| 42-51 | 120 | 0.77 |
| >51 | 140 | 0.77 |

| | 50+ Years, Low IVCD (N = 42) Mean ± SD or % |
|---|---|
| Age (years) | 67.3 ± 9.7 |
| Weight (lb) | 185.1 ± 33.8 |
| Lateral width, level of mid liver (cm) | 37.5 ± 3.9 |
| IV contrast original (ml) | 133.8 ± 22.3 |
| IV contrast new (ml) | 99.6 ± 18.3 |
| Mean IV reduction (ml) | 34.3 ± 6.7 |
| Mean % IV reduction | 26% |
| Reference CTDIvol at 120 kV (mGy) | 19.8 ± 3.0 |
| Actual CTDIvol | 18.4 ± 3.0 |
| 100 kV Used | 55% |
| 120 kV Used | 45% |

Instead of reducing radiation dose (which increases noise), we reduced the iodine contrast dose administered so as to maintain the predicted iodine contrast-noise ratio that would have been achieved had we used a low radiation dose. This protocol was used in patients 50 and older, as in these patients radiation dose is less of a concern, and because patients with renal insufficiency who would benefit from a reduced IVCD usually come from this age group. The older age group (>50) was chosen for this protocol as they are the patients most likely to have renal insufficiency or diabetes and are most likely to benefit from the lower iv contrast dose.

Figure 5:
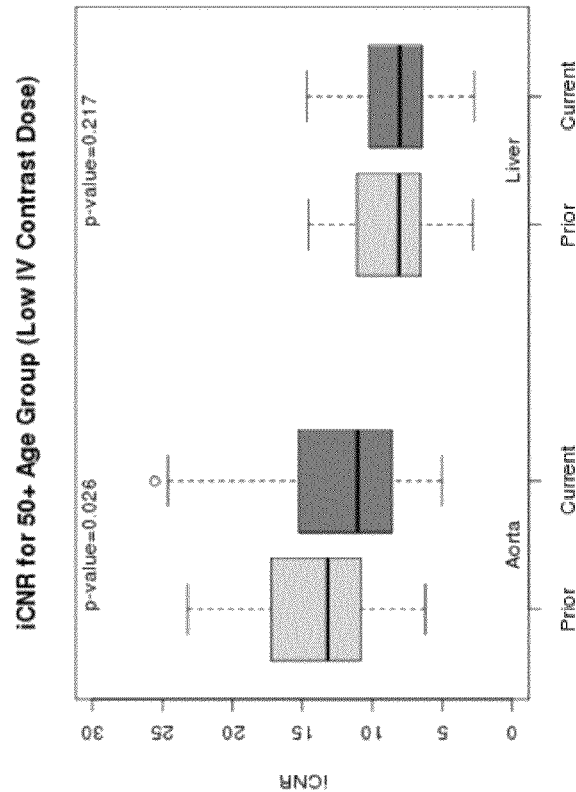
FIG. 5 is a box and whisker plot comparing iCNR in the aorta and liver in the low IVCD scans versus the prior comparison scan, patients 50 years or older.
Figure 4:
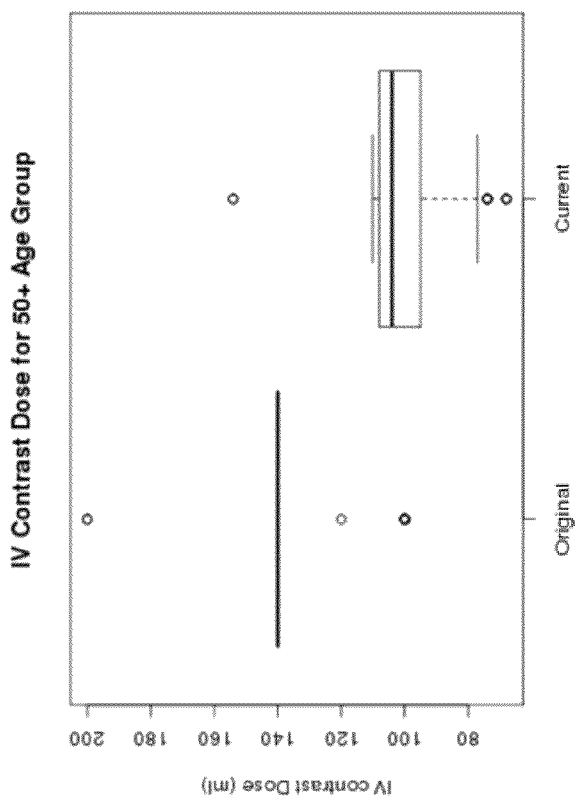
FIG. 4 is a box and whiskers plot of IVCD given on low IVCD scan versus reference contrast dose for routine protocol, patients 50 years or older, low IVCD protocol.

42 patients greater than or equal to 50 years of age were scanned with a mean CTDIvol of 18.4+/−3.0 mGy, not significantly different from the mean reference CTDIvol of 19.8+/−3.0 that would have been given had a routine scan protocol been performed at 120 kV. Mean IVCD administered in this group was 99.6±18.3 ml, versus 133.8+/−22.3 ml had they received routine contrast dose. This represents a mean dose reduction of 26% (p-value<0.001), as illustrated in FIG. 4. Mean IQ for this group was 4.6, versus 4.7 in the prior comparison scan performed with routine IVCD (p=0.273). There was no significant difference in liver iCNR between the study scans and the prior scans, and a 12% decrease in aorta iCNR (p=0.026) on the study scans versus the prior scans, as illustrated in FIG. 5.

It was demonstrated that satisfactory image quality can be obtained with lower radiation dose and/or lower dose of iv contrast in some groups of patients, including those being followed up for lymphoma. By lowering the kV in patients <42 cm lateral width, even greater dose savings can be achieved. In patients aged 50 and older, lower dose of iv contrast is likely to be more beneficial than lower radiation dose. Therefore, it was concluded that this information could serve as the basis for a protocol that should be used in patients 50 years and older.

Figure 6:
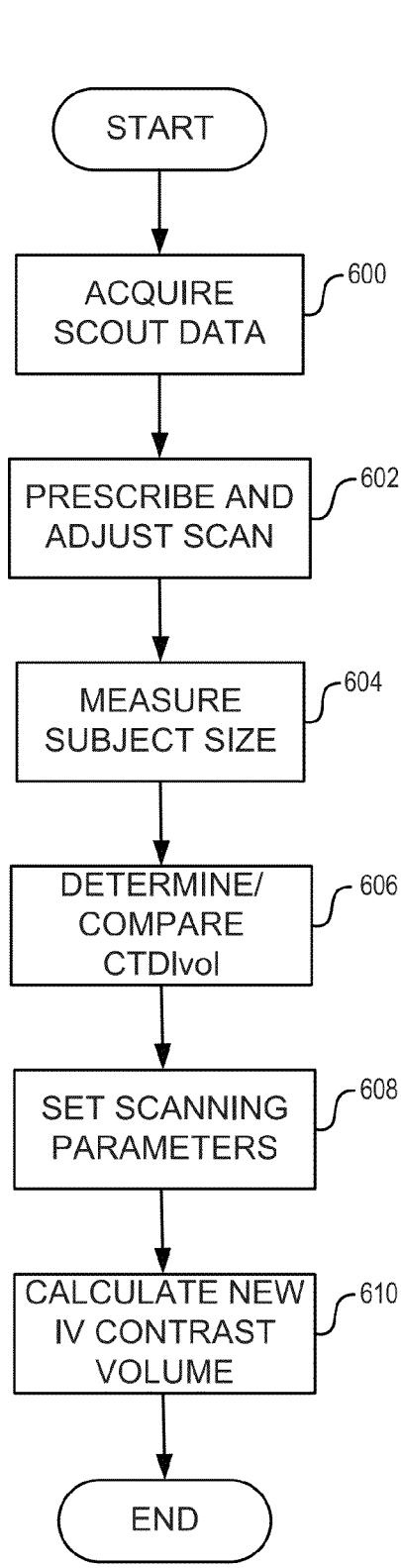
FIG. 6 is a flow chart setting forth steps of a process for conducting an imaging process in accordance with the present invention that controls at least one of a dose of radiation and a dose of a contrast agent.

Referring to FIG. 6, a process in accordance with the present invention and relevant to protocol 1 is illustrated. The process starts at process block 600 with the acquisition of scout data using a scout scan, for example a topogram, and is followed thereafter at process block 602 by prescribing scan protocols at 120 kV and 240 quality reference mAs and adjusting or reducing pitch if necessary to avoid under-estimation of CTDIvol. The CTDIvol is recorded. Then, at process block 604, the size of the subject is measures, for example, by measuring a maximum lateral width at the level of, for example, mid liver. At process block 606, the CTDIvol is determined and compared against a predetermined set of measurements, such as provided above in Table 1 or input into a model consistent with the such measurements to determine the optimal kV and the value of the lowest relative IV contrast. At process block 608, the scanning parameters are adjusted to the optimal kV, along with adjusting the quality reference mAs and pitch to match the recorded CTDIvol. At process block 608, the clinician may consider the projected scanning time and, if too long, adjust the kV to a higher value and repeat the preceding steps for determining optimal kV at process block 606. At process block 610, a new IV contrast volume is calculated by multiplying the original IV contrast volume by the relative IV contrast value determined at process block 606. A standard 50 cc saline chaser will follow at the same rate. By using a size-based kV analysis and keeping the original CTDIvol in the reference technique, IV contrast dose can be lowered to the relative volume shown in the chart above.

Protocol 2, Patients <50 Years

The potential radiation dose that would result in iCNR60% was calculated, taking potential selection of lower kV into account, depending on patient size, such as addressed above in Table 1. No change to IV contrast dose. Low kV and the lowest possible radiation dose, with full IV contrast dose. The younger age group was selected for this protocol as they would benefit the most from the lower radiation dose 17 patients under the age of 50 were scanned with the low radiation dose protocol. The mean CTDIvol was 12.5±4.1 mGy, versus a mean reference CTDIvol of 20.5±4.5 mGy in these patients had they been scanned with routine protocol at 120 kV, with a mean dose reduction of 39% (p<0.001). 11 patients received a dose reduction in excess of 40% and 3 smaller patients received a dose reduction of approximately 50% or more. Mean liver iCNR was 8.6±1.9 versus 9.0±2.1 on the prior scans. Mean aortic iCNR was 13.0±2.7 versus 12.2±2.9 on the prior scans. Mean IQ score was 4.3, versus 5.0 on the prior scans (p-value=0.0005).

This protocol is built off evaluation results from lymphoma patients that showed we can reduce radiation dose by 40%. By further utilizing the dose reduction potential offered by optimal kV, additional radiation dose reduction can be used. This chart and protocol should be used in patients less than 50 years of age.

TABLE 2

| Patient lateral width (cm) - mid liver | Optimal kV | Lowest relative CTDIvol |
|---|---|---|
| 23-29 | 80 | 0.42 |
| 30-35 | 100 | 0.46 |
| 36-41 | 100 | 0.54 |
| 42-51 | 120 | 0.60 |
| >51 | 140 | 0.60 |

| | Under 50 Years, Low radiation dose (N = 17) Mean ± SD or % |
|---|---|
| Age (years) | 40.4 ± 7.7 |
| Weight (lb) | 185.8 ± 28.1 |
| Lateral width, level of mid liver (cm) | 37.1 ± 3.6 |
| Reference CTDIvol at 120 kV (mGy) | 20.5 ± 4.5 |
| Actual CTDIvol used (mGy) | 12.5 ± 4.1 |
| Mean % Dose reduction | 0.39 ± 0.13 |

Figure 7:
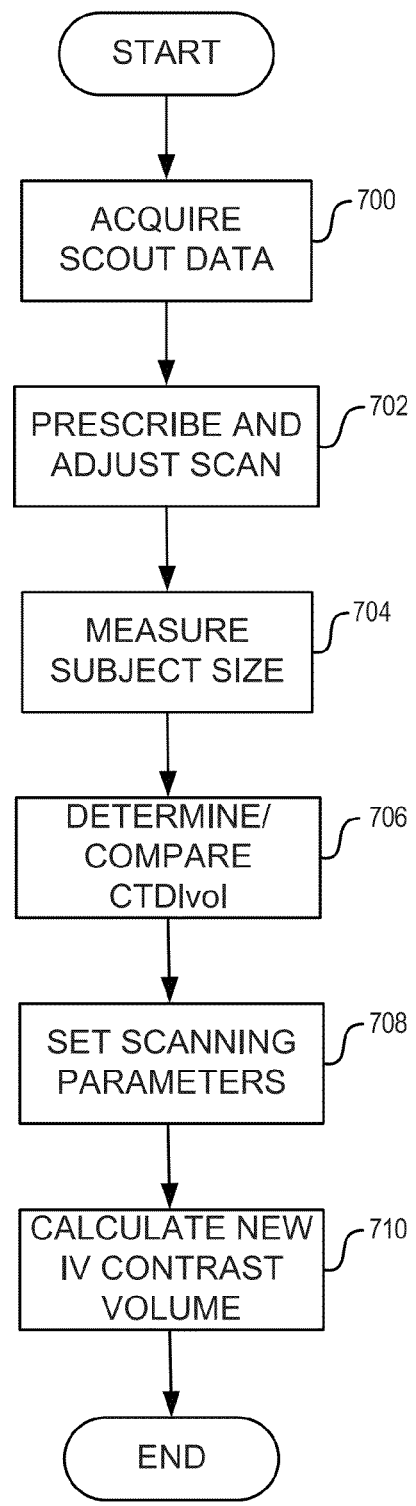
FIG. 7 is a flow chart setting forth steps of another process for conducting an imaging process in accordance with the present invention that controls at least one of a dose of radiation and a dose of a contrast agent.

Referring to FIG. 7, a general process for Protocol 2 is illustrated. The process is similar to that described above with respect to FIG. 6, but relies upon different data or models, such as described above and which is represented by the exemplary embodiment shown in Table 2. The process starts at process block 700 with the acquisition of scout data from a scout scan, such as a topogram, as described above, and is followed thereafter at process block 702 by prescribing scan protocols at 120 kV and 240 quality reference mAs and adjusting or reducing pitch if necessary to avoid under-estimation of CTDIvol. The CTDIvol is recorded. Then, at process block 704, the size of the subject is measures, for example, by measuring a maximum lateral width at the level of, for example, mid liver. At process block 706, the CTDIvol is determined and compared against a predetermined set of measurements, such as provided above in Table 2 or input into a model consistent with the such measurements to determine the optimal kV and the value of the lowest relative IV contrast. At process block 708, the scanning parameters are adjusted to the optimal kV, along with adjusting the quality reference mAs and pitch to match the recorded CTDIvol.

By using a size-based kV reference or model and applying the dose reduction estimated from an evaluation study on simulated low-dose images, radiation dose can be lowered to the relative dose shown in Table 2. Thus, at process block 710, a new IV contrast volume is calculated For the two low-dose protocols, baseline IVCD was calculated according to a default weight-based protocol using Omnipaque 300 (GE Healthcare Inc, Princeton N.J.). Contrast was injected at 3 cc/second, with a scan delay of 70 seconds. Contrast dose (in the over 50 age group) was then altered according to our low-dose protocol, but injection rate and scan delay were not changed. The scans were read in a routine fashion by the radiologist of the day.

There are two parts of possible radiation dose reduction: one is determined from the first phase of the study by evaluating the lowest possible radiation dose from the original protocol at 120 kV; the other is from the optimal kV selection.

Together they represent the total amount of radiation dose that can possibly be reduced while still maintaining the diagnostic quality.

The optimal kV was determined by using a kV technique chart referred to as autokV. The percentage of radiation dose reduction relative to 120 kV were obtained. Since our purpose was not to reduce the radiation dose, we didn't implement this predicted radiation dose reduction in the scan for these patients. Instead, we used the original radiation dose while converting the total amount of allowable radiation dose reduction to IV contrast reduction.

One assumption that is noted is that the iodine CNR given by the lowest-acceptable dose technique established in phase 1 is diagnostically acceptable. Instead of reducing radiation dose (which increases noise), we reduced the dose of iodinated contrast while still maintaining the iodine CNR given by the lowest-acceptable dose technique established in phase 1.

The amount of IV contrast dose reduction can be estimated by calculating the noise decrease due to keeping the original radiation dose relative to the predicted reduced radiation dose. The fundamental assumption is that iCNR60% results in diagnostically acceptable images. The amount of IV contrast dose reduction can be estimated by calculating the noise decrease due to keeping the original radiation dose relative to the predicted reduced radiation dose. If the original CTDIvol at 120 kV is D0 and the estimated CTDIvol after radiation dose reduction is D, then the relative noise $$\frac{\sigma_0}{\sigma} \text{ is } \sqrt{\frac{D_0}{D}}.$$

Therefore, the relative iv contrast dose can be $$\sqrt{\frac{D_0}{D}}$$

in order to maintain the same iCNR.

For example, if the estimated total radiation dose reduction is 40%, then the IV contrast reduction is $(1-\sqrt{0.6}) \times 100 = 22.5\%$. Size-specific charts that took potential changes in radiation dose by changing kV into account were developed, such as provided in the example represented by Table 1.

Optimal kV was determined by patient size. Image quality was measured using the scale used in phase 1, with quantitative noise and CT number measurements additionally performed. Actual IV contrast dose, flow rate, % change in IVCD (from usual protocol), CTDIvol actual, and CTDIvol if 120 kV scanning was performed, were recorded.

In making our comparison with prior scans, we assumed that the IV contrast dose given at the prior scan was the routine dose and flow rate according to our usual contrast protocol. Had the patient's weight or renal function been considerably different at the time of the prior scan, they may have received a greater or lesser dose than the dose we assumed.

IT is contemplated that modifications to the low-IVCD protocol and the low-radiation dose protocol may be desirable in some circumstances. For example the low dose technique works better in scanners with larger detector rows and larger generators, as the tube limit is less likely to be encountered, allowing the use of 100 kV in more patients. Also, on a 128-slice or dual source scanners, 100 kV is used on patients of up to 41 cm width, whereas on a 64-slice scanner 100 kV is used only on patients of <39 cm width. Protocols have been customized for use on Siemens and GE scanners (GE protocol not shown). Different customization may be desirable for other vendors.

Of 17 patients receiving the low radiation dose protocol, 11 patients received a dose reduction in excess of 40% and 3 smaller patients received a dose reduction of approximately 50% or more. The reason that the mean dose reduction was only 39% is at least in part due to human error; in several cases, the technique was not lowered to the full extent allowed. With greater patient numbers, appropriate patient selection and greater technologist experience, we believe that we could more consistently achieve dose reductions of 40-50%. Finally, we believe that addition of noise reduction methods to these images will result in additional incremental radiation dose or intravenous contrast dose savings.

In conclusion, we have demonstrated that with optimized scan protocols and the use of patient size-based low-kV selection it is possible to perform CT of the abdomen and pelvis with substantially lower doses of intravenous contrast or lower radiation doses. Although we chose to implement these studies in patients with lymphoma undergoing follow-up scans, the same protocols could also be used for other clinical indications.

Knowing that additional dose reduction can be achieved by lowering the scan kV, two new body scan protocols were developed, both using a size-specific kV selection. With IRB approval, the following data were recorded on all patients who were scanned with the low dose protocols in whom there was a research authorization in place:

Age, width skin-to-skin at the level of the mid-portion of the liver, measured from the AP topogram, optimal kV as determined by the protocol, actual kV used (in some cases actual kV was higher than optimal kV because scanning with the optimal kV would have exceeded the tube limit of mA). The width skin-to-skin may be measured at the dome of the liver. For patients<50, the CTDIvol at the original reference technique (120 kV, 240 reference mAs) and the CTDIvol using the new protocol was recorded. For patients >50 with the low IVCD protocol, the following were recorded: reference iv contrast dose, actual iv contrast dose, flow rate, percent change in IVCD.

Attenuation measurements were made from each scan and from the most recent prior scan. Attenuation was measured in the aorta at the level of the diaphragm and in the right hepatic lobe at the level of the bifurcation of the main portal vein, avoiding inclusion of hepatic vessels. A region of interest was placed in the anterior subcutaneous fat to measure noise. iCNR was calculated for the aorta and liver according to the formula iCNR=attenuation (HU)/noise in subcutaneous fat (HU). One reader reviewed each abdomen/pelvis scan in random order, blinded to whether is was a study scan or the compare scan, and rated it for image quality on the same 5-point scale that was used in the first phase of the study.

60 patients underwent CT with either reduced IVCD (n=43; patients >50 years) or reduced radiation dose n=17, age <50). 1 patient was excluded from the >50 year group because their prior scan had been performed elsewhere, and the scanning technique was not consistent with our reference protocol.

The 42 patients >50 years were scanned with a mean CTDI vol of 18.4+/−3.0 mGy, not significantly different from the mean reference dose of 19.8+/−3.0 that would have been given had a routine scan protocol been performed. Mean iv contrast dose administered in this group was 99.5±18.5 ml, versus 133.7+/−22.6 cc had they received routine contrast dose. This represents a mean dose reduction of 34%. Mean IQ for this group was 4.6, versus 4.7 in the prior comparison scan performed with routine iv contrast dose (p-value=0.273). There was no significant difference in liver iCNR between the study scans and the prior scans, and a 12% increase in aorta iCNR (p=0.026) on the study scans versus the prior scans.

17 patients under the age of 50 were scanned with low radiation dose. The mean CTDI vol was 12.5±4.1 mGy, versus a mean reference CTDI vol of 20.5±4.5 mGy in these patients had they been scanned with routine protocol at 120 kV, with a mean dose reduction of 39%. Mean liver iCNR was 8.6±1.9 versus 9.0±2.1 on the prior scans. Mean aortic iCNR was 13.0±2.7 versus 12.2±2.9. on the prior scans. Mean IQ score was 4.3, versus 5.0 (p-value=0.0005).

We have shown that with the use of the age-specific protocols, there can be substantial reductions in either IV contrast dose or radiation dose, whilst maintaining diagnostic image quality. We had several reasons for electing to implement the low dose protocols in outpatients with lymphoma undergoing follow-up rather than in other patient groups. Firstly, the lymphoma patients have prior scans available against which we could compare the low dose scans. They tend to be scanned frequently, often at 3-12 month intervals, so they potentially have more to gain from being scanned with either lower radiation dose or lower IV contrast dose than patients undergoing a single scan for an indication such as abdominal pain or weight loss. We chose follow-up scans in lymphoma outpatients rather than other oncology outpatients as we were looking to detect lymphadenopathy and changes in size of lymph nodes, rather than looking for subtle low attenuation lesions in organs such as the liver. We have demonstrated that with the low dose protocols there is satisfactory hepatic enhancement, iCNR and IQ. The protocols are readily amenable to being implemented into routine practice for many indications. Particular instances where the low IVCD protocol are advantageous are any patients at greater risk of contrast induced nephropathy such as patients with renal insufficiency and diabetes, and patients with poor iv access in whom we need good hepatic enhancement yet only a small IV cannula can be placed and a slow injection flow rate used.

We made certain assumptions regarding IV contrast dose. We have standard weight based IV contrast protocols in our practice. When calculating the contrast dose savings on the study scans versus the prior routine full-dose scan, we assumed that the dose given at the prior scan was the routine dose that would have been given according to our usual contrast protocol. Had the patient's weight or renal function been considerably different at the time of the prior scan, they may have received a greater or lesser dose than the dose we assumed. Similarly, it is possible that a patient could have received their injection on the prior scan at a rate slower than our default 3 cc/sec because of poor iv access, and this could negatively impact the enhancement on their prior scan.

We elected to use a saline chaser in the low IVCD patients, whereas in our routine practice we do not use a chaser. It is arguable that we saw no decrease in aortic and hepatic enhancement in our low IVCD patients at least in part due to use of the chaser. However, had we not used a saline chaser our injection duration in the low-IVCD patients the scan duration would have been on average 11 seconds shorter (mean decrease in contrast dose 34 cc/3 cc per sec flow rate), so we may have needed to adjust either our injection rate or scan delay or both to give comparable aortic and hepatic enhancement. By giving the saline chaser we did not need to alter our scan delay. It has been estimated that a saline chaser may result in "savings" of 12-20 ml of contrast in a routine clinical setting, which is somewhat less than the mean 34 mL that we saved. Further, in a recent review of the literature on the use of saline chasers, it was found that a saline chaser does not improve contrast enhancement of the liver in clinical images, and although there was a tendency for improved aortic enhancement, it was not statistically significant.

Based on the findings of the study, it may be desirable to make slight modifications to the low-IVCD protocol for some settings. The protocol works better in scanners with larger detector rows and larger generators, as with these scanners the tube limit is less likely to be encountered, allowing the use of 100 kV in a greater number of patients. For example, on the 128-slice or dual source scanners, we can use 100 kV on patients of up to 41 cm width, whereas on a 64-slice scanner 100 kV is used only on patients of under 39 cm width. Our protocols were customized for use on Siemens scanners and GE scanners (protocol not shown). Different customization may be needed for other vendors.

In patients receiving the low dose protocol, we achieved a mean dose reduction of 39%. This almost equates to the lower dose we could have achieved merely by tolerating more noise, as concluded in the first phase of the study. BY making the additional protocol modifications, in particular, lowering the kV, we would have expected a greater mean dose reduction, of 46-50%. That we did not achieve this much dose reduction is at least in part due to human errors. In several cases, the technologists did not correctly lower the technique to the full extent allowed so the patients did not receive the dose reduction that they could have. We elected not to exclude these patients because our study numbers are small, and because the difficulty experienced by the technologists may accurately reflect the challenge of applying the protocol in a real life situation. With greater patient numbers, appropriate patient selection and greater technologist experience, dose reductions of 40-50% can be achieved more consistently.

In conclusion, we have demonstrated that with optimized scan protocols and the use of patient size-based low-kV selection it is possible to perform CT imaging, for example, of the abdomen and pelvis with substantially lower doses of intravenous contrast or lower radiation doses.

The present invention has been described in terms of one or more preferred embodiments, and it should be appreciated that many equivalents, alternatives, variations, and modifications, aside from those expressly stated, are possible and within the scope of the invention.

The invention claimed is:
1. A method for acquiring an image of a subject using a computed tomography (CT) system, the method comprising:
 a) performing a scout scan of the subject using the CT system to yield scout data;
 b) determining an initial intravenous (IV) contrast volume from at least the scout data;
 c) prescribing a reference scanning protocol for a clinical task to be implemented using the CT system to image the subject;
 d) determining a radiation dose reduction relative to the reference scanning protocol that corresponds to an acceptable image contrast for the clinical task;
 e) determining a reduced intravenous contrast volume associated with the radiation dose reduction using a computed tomography dose index;
 f) adjusting the reference scanning protocol prescribed in step c) using the reduced IV contrast volume determined at step e); and
 g) acquiring imaging data of the subject using the CT system using the adjusted scanning protocol.

2. The method of claim 1 further comprising determining a relative IV contrast value based on a subject characteristic.

3. The method of claim 2 the method further comprising determining the reduced IV contrast volume by multiplying the initial contrast volume by the relative IV contrast value.

4. The method of claim 2 using a subject size, determined from the scout data by measuring a lateral width of the subject, to determine the relative IV contrast value.

5. The method of claim 2 wherein step e) includes accessing a table of reference data relating at least two of subject size, subject age, radiation dose, and IV contrast dose.

6. A computed tomography (CT) imaging system comprising:
- an x-ray source configured to emit x-rays toward an object to be imaged;
- a detector configured to receive x-rays that are attenuated by the object;
- a data acquisition system (DAS) connected to the detector to receive an indication of received x-rays;
- a computer system coupled to the x-ray source and DAS and programmed to:
- control the x-ray source to perform a scout scan of the subject using the CT system and receive scout data related to a region of interest (ROI) from the DAS;
- determine an initial intravenous (IV) contrast volume from at least the scout data;
- prescribe a scanning protocol for a clinical task to image the ROI;
- determine a radiation dose reduction relative to the scanning protocol, wherein the radiation dose reduction corresponds to an acceptable image contrast for the clinical task;
- determine a reduced intravenous contrast volume associated with the radiation dose reduction using a computed tomography dose index;
- update the scanning protocol using the reduced IV contrast volume; and
- control the x-ray source and the DAS using the updated scanning protocol to acquire imaging data from the ROI.

7. The system of claim 6 further wherein the computer is further programmed to determine a relative IV contrast value based on a subject characteristic including a subject size.

8. The system of claim 7 wherein the computer is further programmed to update the scanning protocol by multiplying the initial IV contrast volume by the relative IV contrast value to obtain the reduced intravenous contrast volume.

9. The system of claim 6 wherein the computer is further programmed to receive an indication of a lateral width of the subject extending through the ROI to determine the size of the subject.

10. The system of claim 6 wherein the computer is further programmed to access a table of reference data relating at least two of subject size, subject age, radiation dose, CTDIvol, and IV contrast dose to prescribe the updated scanning protocol.

11. A method for acquiring an image of a subject using a computed tomography (CT) system, the method comprising:
a) performing a scout scan of the subject using the CT system to yield scout data related to at least a region of interest (ROI) of the subject;
b) determining an initial IV contrast volume based on at least one of a clinical task and a subject characteristic;
c) prescribing an initial scanning protocol for the clinical task to be implemented using the CT system to image at least the ROI;
d) determining a radiation dose reduction relative to the initial scanning protocol that corresponds to an acceptable image contrast for the clinical task;
e) selecting, based on the subject characteristic, between the radiation dose reduction and a reduced intravenous contrast volume associated with the radiation dose reduction wherein the reduced intravenous contrast volume is selected using a computed tomography dose index;
f) adjusting the initial scanning protocol prescribed in step c) using the selection at step e); and
g) acquiring imaging data from the ROI using the CT system using the adjusted scanning protocol.

12. The method of claim 11 wherein step f) includes adjusting the scanning protocol prescribed in step c) to match a relative intravenous (IV) contrast dose to a reference IV contrast dose.

13. The method of claim 1 further comprising calculating the reduced IV contrast volume using a relative IV contrast value determined based on the subject characteristic.

14. The method of claim 13 wherein the reduced IV contrast volume is obtained by multiplying the initial contrast volume by the relative IV contrast value.

15. The method of claim 11 wherein step d) includes analyzing attenuation measurements derived from the scout data to determine at least one of a weight of the subject.

16. The method of claim 11 further comprising determining an optimal tube potential to determine a radiation dose reduction.

17. The method of claim 11 further comprising determining a size or an attenuation of the subject about the ROI using the scout data.

18. The method of claim 16, wherein the subject characteristic includes the size of the subject, the attenuation of the subject, a subject age, a subject gender, a subject weight, a subject condition, or a combination thereof.

19. The method of claim 11 further comprising determining a reduced radiation dose value by multiplying an initial dose value by a relative radiation dose value determined based on the subject characteristic.

20. The method of claim 1 further comprising determining an optimal tube potential to determine a radiation dose reduction.

* * * * *

UNITED STATES PATENT AND TRADEMARK OFFICE
CERTIFICATE OF CORRECTION

PATENT NO. : 9,173,617 B2  
APPLICATION NO. : 13/654496  
DATED : November 3, 2015  
INVENTOR(S) : Hough et al.

Page 1 of 1

It is certified that error appears in the above-identified patent and that said Letters Patent is hereby corrected as shown below:

In the Specification

Column 3, line 50 - "SNR noise associated", should be -- SNR associated --

Column 4, line 47 - "if 50", should be -- if $\geq$ 50 --

Column 6, line 9 - "score", should be -- score $\geq 3$ --

Column 6, line 14 - "score", should be -- score $\geq 3$ --

Signed and Sealed this  
Twenty-second Day of March, 2016

Michelle K. Lee  
*Director of the United States Patent and Trademark Office*